Figure 1:
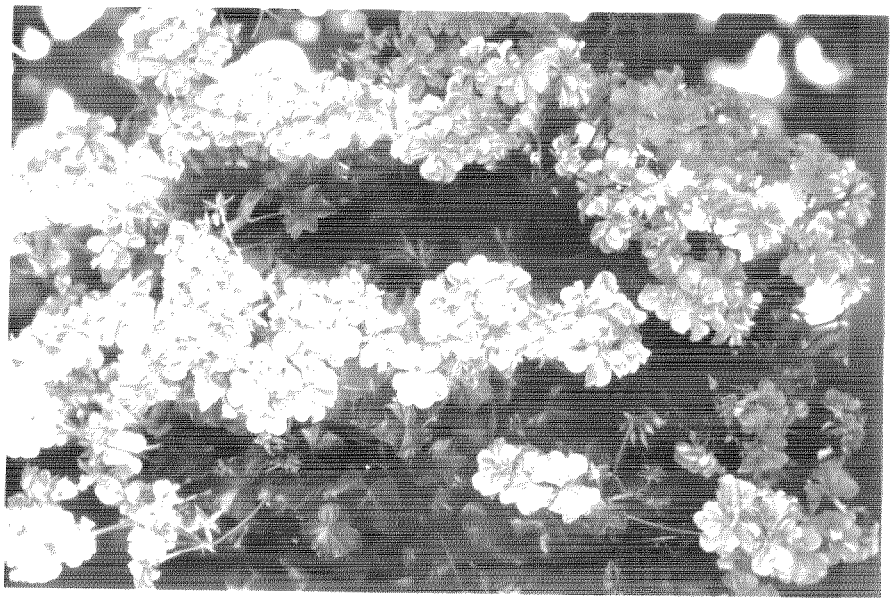

US00PP10380P

United States Patent [19]

Hanes

[11] Patent Number: Plant 10,380

[45] Date of Patent: May 5, 1998

[54] GERANIUM NAMED 'FREE LIGHT LAV'

[75] Inventor: Mitchell Eugene Hanes, Morgan Hill, Calif.

[73] Assignee: Goldsmith Seeds, Inc., Gilroy, Calif.

[21] Appl. No.: 748,267

[22] Filed: Nov. 13, 1996

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Rothwell, Figg, Ernst & Kurz, pc

[57] ABSTRACT

A new geranium cultivar particularly distinguished by green foliage without zonation, light lavender flower color, and semi-double flowers on large umbels, a vigorous plant that is fat rooting with a semi-compact habit.

1 Drawing Sheet

BACKGROUND OF THE NEW PLANT

The present invention comprises a new and distinct cultivar of geranium, botanically known as *Pelargonium peltatum*, and hereinafter referred to by the cultivar name Free Light Lav. The new cultivar is propagated from a seedling resulting from the cross of a seed parent known as 2581-3 and by using the ivy geranium known as Amethyst (not a patented variety) as the pollen parent.

Free Light Lav is a product of a planned breeding program intended to create new ivy geranium cultivars with light lavender colored flowers, semi-double flower form, mid-green foliage, vigorous growth and superior cutting productivity.

The new cultivar was created in 1922 in Gilroy, Calif. and has been repeatedly asexually reproduced by cuttings in Gilroy, Calif. and Guatemala over a four year period. It has also been trailed at Okemos, Mi. It has been found to retain its distinctive characteristics through successive propagations; and this novelty appears to be firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit;

DESCRIPTION OF THE NEW CULTIVAR

The following detailed descriptions set forth the distinctive characteristics of Free Light Lav . The data which defines these characteristics were collected from asexual reproductions carried out by Goldsmith Seeds, Inc. in Gilroy, Calif. The plant histroy was taken on 18 week old plants, blossomed under natural light in a greenhouse and color readings were taken in the greenhouse (in Gilroy, Calif.) on Aug. 29, 1996 under ambient light. Color references are primarily to the R.H.S. Colour Chart of The Royal Horticultural Society of London (R.H.S).

The Plant

Classification:

*Botanical.—Pelargonium peltatum.*

*Commercial.*—Ivy geranium.

Form: Compact free branching plant.

Height: 11 cm, as a 4½inch pot plant, excluding blooms.

Growth: Rounded growth habit with short internodes.

Strength: Green shiny foliage. Good shipping ability as rooted or unrooted cuttings.

Foliage: Abundant quantity.

*Leaves.*—Size: Diameter about 5 cm. Shape: Ivy-shaped leaf with edges raised above the plane of the center of the leaf. Margin: Smooth. Texture: Waxy on both surfaces. Ribs: Radiate from the point of attachment of the petiole. Veins: Present but very inconspicuous. Color: Upper side: Green Under side: Lighter green color. Veins a little more distinct that on the upper leaf surface. Petioles: About 2.5 to 3.5 cm in length on a mature leaf.

The Bud

Size:

*Diameter.*—About 10 mm.

*Length.*—About 1.9 cm at time of bud opening.

Shape: Pointed ovoid.

Color: Petals when sepals first divide is 81B, R.H.S.

Sepals: 5 in number, flat behind petals. Pointed linear lanceolate, 146D R.H.S. in an open flower.

The Flower

Blooming habit: Continuous throughout the year.

Size: Approximately 4.8–5.1 cm diameter, 1.7 cm deep.

Form: Semi-double.

Petals: Color 81C RHS. Approximately 7 imbricate outer petals, 1.6–1.8 cm wide and approximately 2.3 cm long. Six to eight inner smaller petaloids of varying shape. Both the outer petals and inner petaloids are light lavender from the base of the petal to the outer margin. The two top petals have a feather vein pattern that is (a darker rose purple color) 74A RHS. Veins slightly darker than interveinal regions. Color changing little with age. Underside of petals lighter. Petals and petaloids soft and satiny.

Pedicel: Approximately 2.6cm in length

Persistence: Non-shattering flower.

Inflorescence

Type: An umbel composed of approximately 10 flowers, erect or laterally ascending.

Peduncle: Approximately 9.5 cm in length, green without pigmentation.

Reproductive Organs

Stamens:

*Anthers.*—8–10 positioned below the mature stigma, dull red prior to anthesis.

*Filaments.*—White.

*Pollen.*—Orange in color.

Pistil:

*Number.*—1.

*Length.*—Approximately 10 mm.

*Stigma.*—5 linear lobes of near equal length, curling back toward ovary, purplish-red.

*Style.*—Length: About 5 mm. Color: White.

*Ovaries.*—At anthesis, densely pubescent with white hairs, oblong. Green drying to a light brown at maturity.

*Fruit.*—Partially fertile.

I claim:

1. A new and distinct cultivar of geranium plant substantially as herein shown and described, named Free Light Lav, that is characterized by: green foliage without zonation, light lavender flower color, and semi-double flowers on large umbels, a vigorous plant that is fast rooting with a semi-compact habit.

* * * * *